(12) United States Patent
Zhang et al.

(10) Patent No.: US 8,996,101 B2
(45) Date of Patent: *Mar. 31, 2015

(54) HEART SOUND SENSING TO REDUCE INAPPROPRIATE TACHYARRHYTHMIA THERAPY

(75) Inventors: Xusheng Zhang, Shoreview, MN (US); Teresa A. Whitman, Dayton, MN (US); Paul J. DeGroot, Shoreview, MN (US); Mark L. Brown, North Oaks, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/457,983

(22) Filed: Apr. 27, 2012

(65) Prior Publication Data

US 2013/0237873 A1 Sep. 12, 2013

Related U.S. Application Data

(60) Provisional application No. 61/609,452, filed on Mar. 12, 2012.

(51) Int. Cl.
| | | |
|---|---|---|
| *A61B 5/0464* | (2006.01) | |
| *A61B 5/00* | (2006.01) | |
| *A61N 1/365* | (2006.01) | |
| *A61N 1/362* | (2006.01) | |
| *A61B 5/046* | (2006.01) | |

(52) U.S. Cl.
CPC .......... *A61B 5/7221* (2013.01); *A61N 1/36514* (2013.01); *A61N 1/3621* (2013.01); *A61B 5/0464* (2013.01); *A61B 5/046* (2013.01)

USPC .............. 600/513; 607/6; 607/14; 607/27; 600/518; 600/528

(58) Field of Classification Search
None
See application file for complete search history.

(56) References Cited

U.S. PATENT DOCUMENTS

| | | | |
|---|---|---|---|
| 4,374,382 A | | 2/1983 | Markowitz |
| 5,085,215 A | * | 2/1992 | Nappholz et al. ............... 607/17 |
| 5,097,830 A | * | 3/1992 | Eikefjord et al. ................ 607/8 |
| 5,117,824 A | | 6/1992 | Keimel |
| 5,144,949 A | * | 9/1992 | Olson ............................. 607/17 |
| 5,205,283 A | * | 4/1993 | Olson ............................. 607/4 |
| 5,350,409 A | * | 9/1994 | Stoop et al. .................... 607/17 |
| 5,480,412 A | * | 1/1996 | Mouchawar et al. ............ 607/6 |
| 5,545,186 A | | 8/1996 | Olson |
| 5,755,736 A | | 5/1998 | Gillberg |
| 5,873,897 A | * | 2/1999 | Armstrong et al. ............. 607/14 |
| 6,393,316 B1 | | 5/2002 | Gillberg |
| 6,869,404 B2 | | 3/2005 | Schulhauser |
| 7,130,681 B2 | | 10/2006 | Gebhardt |
| 7,682,316 B2 | | 3/2010 | Anderson |
| 7,783,354 B2 | | 8/2010 | Gunderson |

(Continued)

*Primary Examiner* — Kennedy Schaetzle
(74) *Attorney, Agent, or Firm* — Michael C. Soldner

(57) ABSTRACT

A method and device for detecting a cardiac event that includes sensing cardiac electrical signals representative of electrical activity of a heart of a patient, detecting the cardiac event in response to the sensed cardiac signals, determining an indication of signal reliability corresponding to the sensed cardiac signals as being one of a reliable signal and a not reliable signal, and switching operation of the device between a first mode of determining whether the sensed signal is one of treatable and not treatable and a second mode of determining whether the sensed signal is one of treatable and not treatable in response to the determined indication of signal reliability.

21 Claims, 10 Drawing Sheets

(56) References Cited

U.S. PATENT DOCUMENTS

| | | |
|---|---|---|
| 7,831,304 B2 | 11/2010 | Cao |
| 7,904,153 B2 | 3/2011 | Greenhut |
| 2002/0120307 A1* | 8/2002 | Jorgenson et al. ............... 607/27 |
| 2003/0144705 A1* | 7/2003 | Funke .............................. 607/27 |
| 2004/0127792 A1 | 7/2004 | Siejko |
| 2006/0020294 A1* | 1/2006 | Brockway et al. ............... 607/17 |
| 2006/0116733 A1* | 6/2006 | Gunderson ...................... 607/27 |
| 2007/0142866 A1 | 6/2007 | Li |
| 2008/0125820 A1 | 5/2008 | Stahmann |
| 2009/0204163 A1* | 8/2009 | Shuros et al. ................... 607/14 |
| 2009/0264716 A1 | 10/2009 | Shuros |
| 2010/0185109 A1 | 7/2010 | Zhang |
| 2010/0217143 A1 | 8/2010 | Whittington |
| 2010/0331903 A1 | 12/2010 | Zhang |
| 2011/0196247 A1 | 8/2011 | Cao |
| 2011/0301473 A1* | 12/2011 | Wariar et al. .................. 600/486 |
| 2012/0016249 A1 | 1/2012 | Lian |
| 2013/0237872 A1* | 9/2013 | Zhang et al. ................... 600/513 |

\* cited by examiner

HEART SOUND SENSING TO REDUCE INAPPROPRIATE TACHYARRHYTHMIA THERAPY

CROSS-REFERENCE TO PRIORITY APPLICATION

The present application claims priority and other benefits from U.S. Provisional Patent Application Ser. No. 61/609,452, filed Mar. 12, 2012, incorporated herein by reference in its entirety.

FIELD OF THE DISCLOSURE

This disclosure relates to medical devices and, more particularly, to medical devices that delivery therapy to terminate tachyarrhythmias.

BACKGROUND

Medical devices, such as implantable cardioverter-defibrillators, provide therapeutic electrical stimulation to the heart in order to terminate tachyarrhythmia, such as tachycardia or fibrillation. The electrical stimulation may include signals such as pulses or shocks for pacing, cardioversion or defibrillation. In some cases, the medical device may sense intrinsic depolarizations of the heart, detect tachyarrhythmia based on the intrinsic depolarizations, and control delivery of electrical stimulation to the heart if tachyarrhythmia is detected based on the intrinsic depolarizations.

Medical devices sense cardiac electrical signals and deliver therapeutic stimulation via electrodes. Implantable pacemakers, cardioverters, defibrillators, or pacemaker-cardioverter-defibrillators are typically coupled to one or more intracardiac leads that carry electrodes for cardiac sensing and delivery of therapeutic stimulation. The cardiac electrical signals sensed via the electrodes may be referred to as a cardiac electrogram (EGM). In some systems, electrodes positioned outside the heart, for example in subcutaneous or submuscular locations are used to sense electrocardiogram (ECG) signals. The cardiac electrical signals include depolarizations and other intrinsic electrical activity of the heart.

In some cases, a medical device delivers therapeutic electrical stimulation, such as a defibrillation pulse, when the stimulation is not required. Delivery of such therapy by a medical device is often due to misinterpretation of the cardiac EGM (or ECG) as indicating a rapid or unstable ventricular tachycardia or ventricular fibrillation. In some cases, the medical device detects a rapid ventricular tachycardia or ventricular fibrillation when the cardiac rhythm is in fact stable, or otherwise not requiring a defibrillation pulse, such as sinus tachycardia (ST), supraventricular tachycardia (SVT), or rapid atrial tachycardia/atrial fibrillation (AT)/(AF) conducted to the ventricles, or a hemodynamically stable ventricular tachycardia (VT). In some cases, the medical device misinterprets T-waves in the cardiac EGM as R-waves, which is referred to as T-wave over-sensing (TWOS), and may cause the medical device to interpret the cardiac rhythm as having a higher ventricular rate than the actual rate. In some cases, the medical device over-senses R-waves due to non-physiological or non-cardiac signals in the cardiac EGM, which may be the result of electromagnetic interference (EMI), EGM clipping, lead fracture, or muscle noise, as examples. Implantable medical devices that detect the cardiac EGM via implantable medical leads may be susceptible to oversensing due to non-physiological or non-cardiac signals in the cardiac EGM.

DETAILED DESCRIPTION

The techniques described in this disclosure allow a medical device to use a heart sound signal to reduce inappropriate delivery of tachyarrhythmia therapy. Analysis of heart sound signals may reduce inappropriate delivery of therapy because heart sounds provide complementary information that can be used to corroborate EGM based decisions when the EGM signal is reliable. In addition, heart sounds are not susceptible to the same noise sources or other misinterpretation issues as EGMs. For example, the heart sound sensor may be more immune to noise that negatively effects EGMs, such as EMI, lead fracture, and muscle noise. As such, heart sound signals may be relied upon for therapy decisions when the EGM signal is determined to be unreliable.

In general, heart sounds are associated with mechanical vibrations of a patient's heart and the flow of blood through the heart and, thus, are highly correlated with pressure gradients across heart valves and blood pressure. Heart sounds are not only due to vibrations of and pressure within the heart, but may be due to the whole cardiohemic system, e.g., blood, heart, great arteries, etc. Heart sounds recur with each cardiac cycle and are separated and classified according to the activity associated with the vibration. The first heart sound is referred to as "S1," and can be thought of as the vibrational sound made by the heart during closure of the atrioventricular (AV) valves, i.e., the mitral valve and tricuspid valve. The second heart sound is referred to as "S2," and results from the closure of the semilunar valves, i.e., the pulmonary and aortic valves. The S2 heart sound can be thought of as marking the beginning of diastole. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

The described techniques may enhance specificity with minimal impact on sensitivity. In particular, the described techniques may successfully withhold an incorrect EGM based decision that a rhythm is treatable with a therapy, such as defibrillation, and not withhold a correct EGM based decision that a rhythm is a treatable ventricular tachycardia (VT) or ventricular fibrillation (VF).

Additionally, a heart sound sensor, such as a piezoelectric sensor or other acoustic sensor, may be easy to implement with an implantable medical device (IMD), e.g., on a lead or within a housing of the IMD. Enclosing the sensor within the housing of the IMD may provide additional protection for the sensor.

Figure 1:
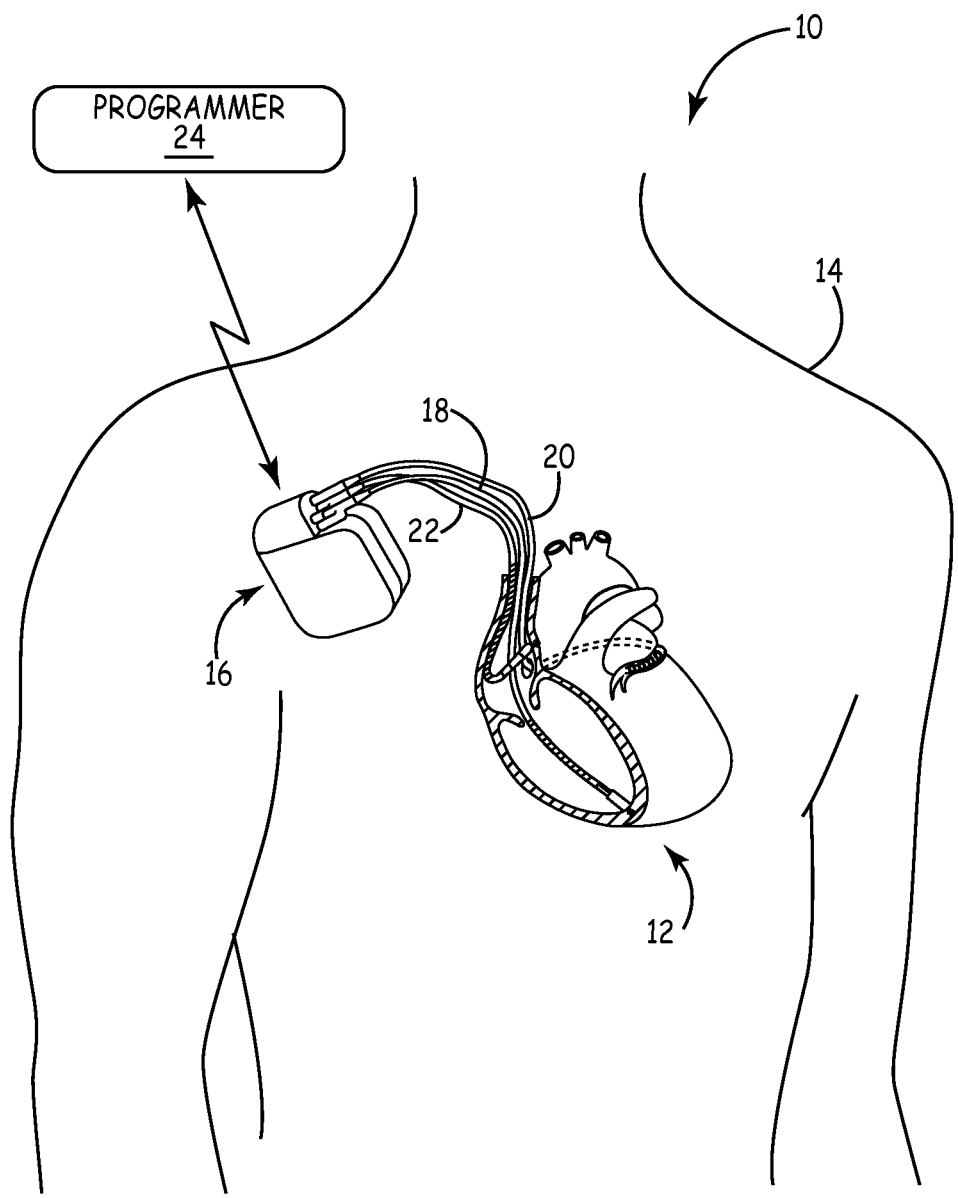
FIG. 1 is a conceptual diagram illustrating an example system that detects heart sounds to reduce inappropriate delivery of tachyarrhythmia therapy to a patient.

FIG. 1 is a conceptual diagram illustrating an example system 10 that detects heart sounds to reduce inappropriate delivery of tachyarrhythmia therapy to patient 14. In particular, system 10 determines whether a cardiac rhythm of patient 14 is treatable based, at least in part, on detected heart sounds of the patient. In some examples, system 10 may first determine whether a cardiac rhythm is treatable or non-treatable based on a cardiac EGM. The system then determines whether the EGM signal is reliable. Based on the EGM reliability, the system selects a heart sound analysis algorithm to confirm the rhythm determination based on monitored heart sounds of patient 14. For example, if the EGM is found unreliable, e.g. due to noise corruption or oversensing, detection of heart sounds and analysis of heart sound data is performed independent of the EGM signal. If the EGM signal is found reliable, acquisition and analysis of heart sound data is performed dependent on the EGM signal, e.g. using EGM-gated ensemble averaging. Based on detected heart sounds, system 10 may confirm a tachyarrhythmia detection and deliver the therapy to patient 14, or deny the detection and withhold the therapy. Determining whether a rhythm is treatable or non-treatable based on both EGM and heart sounds may reduce inappropriate delivery of tachyarrhythmia therapy to patient 14.

System 10 includes implantable medical device (IMD) 16, which is connected to leads 18, 20, and 22, and communicatively coupled to a programmer 24. IMD 16 senses electrical signals attendant to the depolarization and repolarization of heart 12, e.g., a cardiac EGM, via electrodes on one or more of leads 18, 20 and 22 or a housing of IMD 16. IMD 16 also delivers therapy in the form of electrical signals to heart 12 via electrodes located on one or more leads 18, 20, and 22 or a housing of IMD 16, such as pacing, cardioversion and/or defibrillation pulses. IMD 16 also includes, or is coupled to via one or more of leads 18, 20 and 22, one or more heart sound sensors (not shown in FIG. 1). IMD 16 may similarly include or be coupled to other sensors, such as one or more accelerometers, for detecting other physiological parameters of patient 14, such as activity or posture.

In some examples, programmer 24 takes the form of a handheld computing device, computer workstation, or networked computing device that includes a user interface for presenting information to and receiving input from a user. A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

In some embodiments programmer 24 may be coupled to a server via a communication network to enable a user to interact with programmer 24 remotely using a computing device coupled to the server. Examples of such a system and network configuration including IMD 16 and programmer 24 are described in the above-referenced U.S. Publication No. 2010/0331903.

IMD 16 and programmer 24 communicate via wireless communication. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24. IMD 16 is shown in a right pectoral implant position in FIG. 1, but may alternatively be implanted in a left pectoral position. In other examples, programmer 24 may be located remotely from IMD 16, and communicate with IMD 16 via wireless distance telemetry or a network.

As will be described in greater detail, IMD 16 may deliver or withhold therapeutic stimulation or "therapy" to patient 14 for terminating a tachyarrhythmia of heart 12 based, at least in part, on heart sounds. Examples of tachyarrhythmias include ventricular tachycardia and ventricular fibrillation. Examples of therapeutic stimulation to terminate tachyarrhythmia include pacing, e.g., anti-tachycardia pacing (ATP), cardioversion shocks and defibrillation shocks.

The techniques for reducing inappropriate therapy based on heart sounds are primarily described herein as being performed by IMD 16, e.g., by a processor of IMD 16. In other examples some or all of the functions ascribed to IMD 16 or a processor thereof may be performed by one or more other devices, such as programmer 24, or a processor thereof. For example, programmer 24 may process heart sound and/or EGM signals received from IMD 16 to determine whether a therapy should be delivered to terminate a tachyarrhythmia, and control whether IMD 16 delivers the therapy. Furthermore, although described herein with respect to an IMD, in other examples, the techniques described herein may be performed by or implemented in an external medical device, which may be coupled to a patient via percutaneous or transcutaneous leads.

Figure 2:
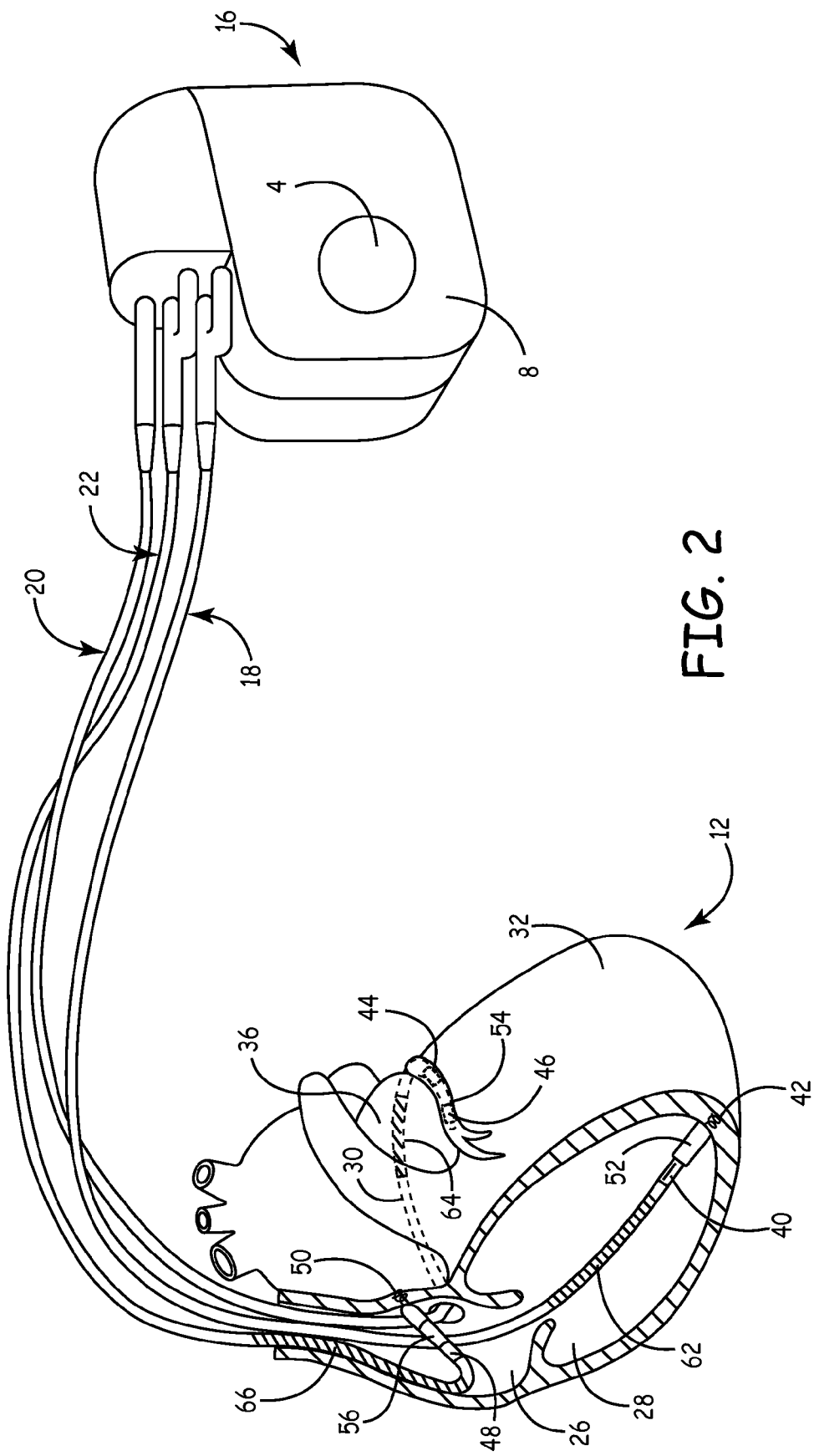
FIG. 2 is a conceptual diagram illustrating the implantable medical device (IMD) and leads of the system of FIG. 1 in greater detail.

FIG. 2 is a conceptual diagram illustrating IMD 16 and leads 18, 20, and 22 of system 10 in greater detail. In the illustrated example, bipolar electrodes 40 and 42 are located adjacent to a distal end of lead 18 advanced into the right ventricle (RV) 28 of heart 12. In addition, bipolar electrodes 44 and 46 are located adjacent to a distal end of lead 20 shown advanced into a cardiac vein 30 via the coronary sinus in the right atrium (RA) 26. Lead 20 is used for sensing EGM signals and delivering therapy in the left ventricle (LV) 32. Bipolar electrodes 48 and 50 are located adjacent to a distal end of lead 22, positioned in the RA 26.

In the illustrated example, electrodes 40, 44 and 48 take the form of ring electrodes, and electrodes 42, 46 and 50 may take the form of extendable helix tip electrodes optionally mounted retractably within insulative electrode heads 52, 54 and 56, respectively. Leads 18, 20, 22 also include elongated electrodes 62, 64, 66, respectively, which may take the form of a coil. Each of the electrodes 40, 42, 44, 46, 48, 50, 62, 64 and 66 is electrically coupled to a respective conductor within the lead body of its associated lead 18, 20, 22, and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other division between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a heart sound sensor that generates an electrical signal based on sensed heart sounds. The heart sound sensor may be enclosed within housing 8. Alternatively, the heart sound sensor may be integrally formed with an outer surface of housing 8, carried on a lead coupled to IMD 16, such as one or more leads 18, 20 and 22, or be a remote sensor that wirelessly communicates with IMD 16, programmer 24, or any other device described herein.

IMD 16 senses electrical signals attendant to the depolarization and repolarization of heart 12 via any of electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 4 in a unipolar configuration. Furthermore, IMD 16 may deliver cardioversion or defibrillation pulses to heart 12 via any combination of elongated electrodes 62, 64, 66, and housing electrode 4.

The illustrated numbers and configurations of leads 18, 20, and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more epicardial or subcutaneous leads not positioned within the heart. As another example, system 10 may include an additional lead that carries a heart sound sensor positioned such that signals generated by the heart sound sensor include heart sounds. In some embodiments, a device for sensing cardiac electrical signals, heart sounds, and delivering cardioversion/defibrillation pulses in response to treatable tachyarrhythmia detection is a subcutaneous system including housing electrodes and/or subcutaneous leads and electrodes without the use of transvenous leads, electrodes or other sensors. An example of such a system is generally disclosed in commonly-assigned U.S. Pat. No. 7,904,153 (Greenhut et al.), hereby incorporated herein by reference in its entirety.

Figure 3:
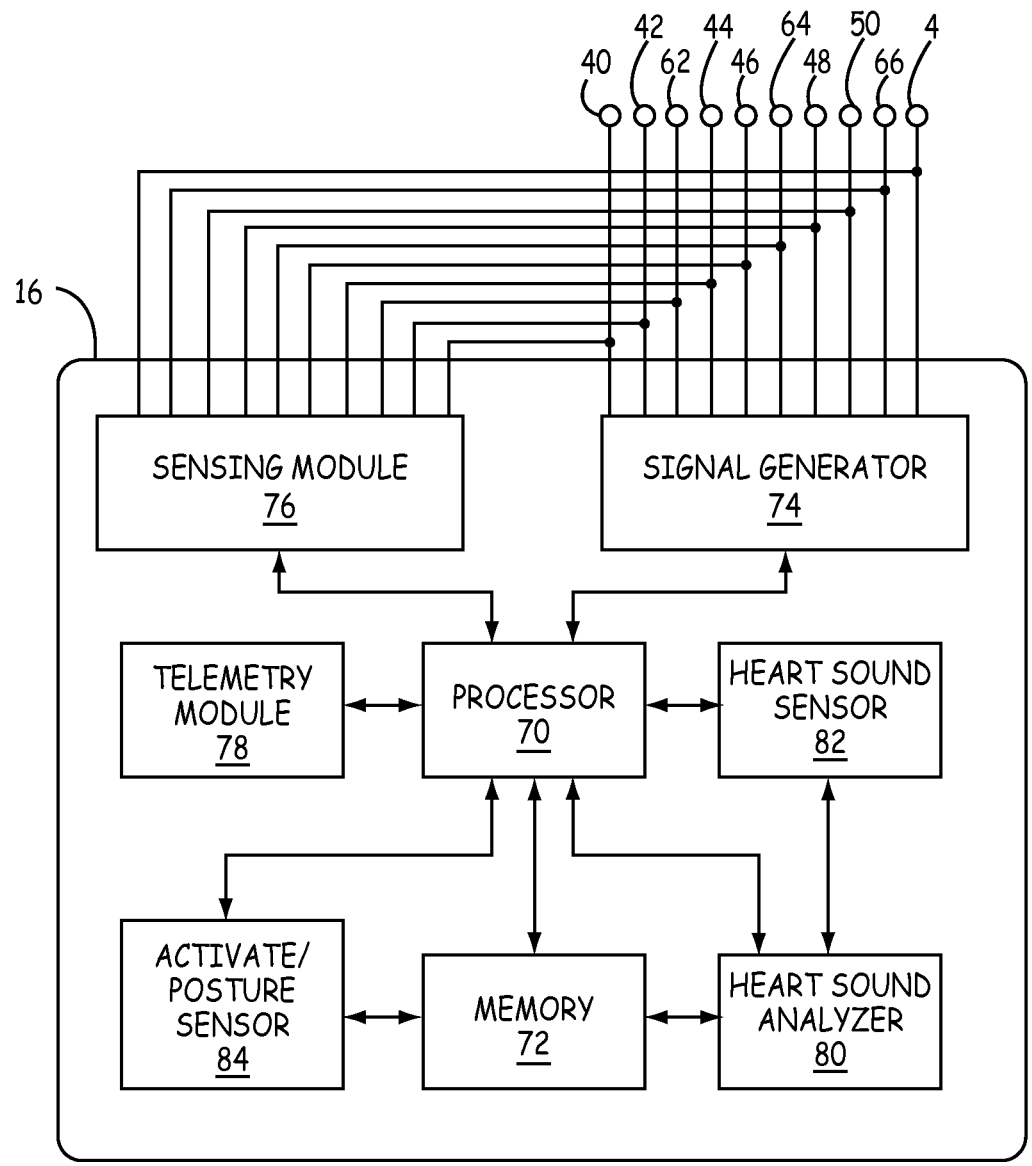
FIG. 3 is a block diagram illustrating an example configuration of the IMD of FIG. 2.

FIG. 3 is a block diagram illustrating an example configuration of IMD 16. In the illustrated example, IMD 16 includes a processor 70, memory 72, signal generator 74, sensing module 76, telemetry module 78, heart sound analysis module 80 (also referred to herein as (heart sound analyzer")), heart sound sensor 82 and activity and/or posture sensor 84. Memory 72 includes computer-readable instructions that, when executed by processor 70, causes IMD 16 and processor 70 to perform various functions attributed to IMD 16 and processor 70 herein. The computer-readable instructions may be encoded within memory 72. Memory 72 may include any volatile, non-volatile, magnetic, optical, or electrical computer-readable storage media, such as a random access memory (RAM), read-only memory (ROM), non-volatile RAM (NVRAM), electrically-erasable programmable ROM (EEPROM), flash memory, or any other digital computer-readable media with the sole exception being a transitory propagating signal.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs.

Signal generator 74 is configured to generate and deliver electrical stimulation therapy to patient 12. As shown in FIG. 3, signal generator 74 is electrically coupled to electrodes 4, 40, 42, 44, 46, 48, 50, 62, 64, and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64, and 66. In other examples, signal generator 74 delivers stimulation in the form of signals other than pulses, such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes.

Electrical sensing module 76 monitors electrical cardiac signals from any combination of electrodes 4, 40, 42, 44, 46, 48, 50, 62, 64, and 66. Sensing module 76 may also include a switch module which processor 70 controls to select which of the available electrodes are used to sense the heart electrical activity, depending upon which electrode combination is used in the current sensing configuration. Sensing module 76 may include one or more sensing channels, each of which may comprise an amplifier, for sensing different cardiac electrical signals. Some sensing channels may sense events, such as R-waves or P-waves, and provide indications of the occurrences of such events to processor 70. One or more other sensing channels may provide the signals to an analog-to-digital converter, for conversion into a digital signal for processing or analysis by processor 70.

For example, sensing module 76 may comprise one or more narrow band channels, each of which may include a narrow band filtered sense-amplifier that compares the signal to a threshold. If the filtered and amplified signal is greater than the threshold, the narrow band channel indicates that a certain electrical cardiac event, e.g., depolarization, has occurred, i.e. "sensed". Processor 70 then uses that sensed event in measuring frequencies of the sensed events for detecting tachyarrhythmias.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 (Keimel et al.).

In some examples, sensing module 76 includes a wide band channel which may comprise an amplifier with a relatively wider pass band than the narrow band channels. Signals from the electrodes that are selected for coupling to this wide-band amplifier may be converted to multi-bit digital signals by an analog-to-digital converter (ADC) provided by, for example, sensing module 76 or processor 70. Processor 70 may analyze the digitized versions of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of numerous signal processing methodologies. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. A stored interval length may need to be detected for a certain number of consecutive cycles, for a certain percentage of cycles within a running window, or a running average for a certain number of cardiac cycles, as examples. The number of intervals required to meet tachycardia or fibrillation detection is referred to as a "number of intervals to detect" or NID and may be expressed as the number of intervals meeting the detection interval length out of a consecutive number of intervals, e.g. 8 out of 10 intervals.

A tachyarrhythmia detection method may include any suitable tachyarrhythmia detection algorithms. For example, EGM morphology may be considered in addition to or instead of interval length for detecting tachyarrhythmias. In one example, processor 70 may utilize all or a subset of the rule-based detection methods described in U.S. Pat. No. 5,545,186 (Olson, et al.) and U.S. Pat. No. 5,755,736 (Gillberg et al.), both of which patents are incorporated herein by reference in their entireties. However, other tachyarrhythmia detection methodologies may also be employed by processor 70.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM.

To avoid or reduce delivery of therapy in response to a mistakenly classified EGM, IMD 16 also includes heart sound sensor 82 and heart sound analyzer 80. Heart sound sensor 82 generates an electrical signal representative of heart sounds of patient 14, and may be implemented as a piezoelectric sensor, a microphone, an accelerometer, or other type of acoustical sensor. In some examples, heart sound sensor 82 may comprise more than one sensor. For example, heart sound sensor 82 may comprise multiple accelerometer devices.

In the illustrated example, heart sound sensor 82 is enclosed within housing 8 of IMD 16. In some examples, heart sound sensor 82 may be formed integrally with an outer surface of housing 8. In other examples, heart sound sensor 82 is located on a lead that is coupled to IMD 16 or may be implemented as a remote sensor that wirelessly communicates with IMD 16. In any case, heart sound sensor 82 is electrically or wirelessly coupled to circuitry contained within housing 8 of IMD 16.

Heart sound analyzer 80 receives the electrical signal generated by heart sound sensor 82. In one example, heart sound analyzer 80 processes the sensor signal to detect heart sounds, classifies the detected heart sounds as either normal or abnormal, and generates an indication that the heart rhythm of the patient is either treatable or non-treatable based on the classification of one or more of the detected heart sounds. In one example, heart sound analyzer 80 processes the sensor signal to generate an envelope signal independent of EGM or ECG signals, applies an algorithm that uses an adaptively decaying threshold to detect heart sounds within the envelope signal, extracts heart sound features from the detected heart sounds, and classifies the detected heart sounds as normal or abnormal based on the heart sound features. In another example, heart sound analyzer 80 processes the sensor signal to generate an ensemble averaged heart sound signal using a cardiac electrical signal, e.g. the EGM signal, for selecting and aligning heart sound signal intervals, then extracts the heart sound features from the ensemble averaged signal. The operation of heart sound analyzer 80 in an EGM-dependent or EGM-independent manner is controlled based on a determination of the reliability of the EGM signal by processor 70. The operation of heart sound analyzer 80 in accordance with these example methods is described in greater detail with respect to FIGS. 4-10. In any case, the heart sound based indication of a treatable or non-treatable rhythm may be output to processor 70, which may allow or withhold the a tachyarrhythmia therapy based on the indication.

In some examples, IMD 16 performs these steps prior to delivering any therapy, such as anti-tachycardia pacing (ATP), to the heart of the patient. In other examples, IMD 16 analyzes heart sounds or other aspects of the heart sound signal during delivery of pacing pulses, e.g., ATP. For example, IMD 16 may classify the cardiac rhythm as treatable or non-treatable based on whether the delivery of pacing pulses results in heart sounds that are classified as normal, and selectively deliver or withhold therapy, such as cardioversion or defibrillation, based on the classification. In some examples, IMD 16 delivers the electrical pulses, e.g., ATP, during confirmation phase of tachyarrhythmia detection. In other examples, IMD 16 may deliver ATP to the patient in response to heart sound analyzer 80 indicating that the heart rhythm is treatable based on an analysis of unpaced heart sounds.

Although processor 70 and heart sound analyzer 80 are illustrated as separate modules in FIG. 3, processor 70 and heart sound analyzer 80 may be incorporated in a single processing unit. Heart sound analyzer 80, and any of its components discussed in greater detail below, may be a component of or module executed by processor 70.

Furthermore, the components of and functionality provided by a heart sound analyzer 80 are described herein with respect to examples in which heart sound analyzer 80 is located within IMD 16. However, it is understood that any one or more heart sound analyzers 80 may be individually or collectively provided by any one or more devices, such as IMD 16 and programmer 24 or another computing device communicatively coupled to programmer 24, to individually or collectively provide the functionality described herein. Programmer 24 may receive signals generated by heart sound sensor 4 from IMD 16 in embodiments in which programmer 24 includes a heart sound analyzer.

As illustrated in FIG. 3, IMD 16 may also include an activity and/or posture sensor 84. Activity and/or posture sensor 84 may, for example, take the form of one or more accelerometers, or any other sensor for detecting activity, e.g., body movement or footfalls, or posture. In some examples, activity and/or posture sensor 84 may comprises a three-axis accelerometer. In some examples, heart sound sensor 82 and activity and/or posture sensor 84 may comprise one or more common accelerometers.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., EGM signals, acquired by sensing module 76 and/or signals generated by heart sound sensor 82 to programmer 24. Processor 70 may also generate and store marker codes indicative of different cardiac events that sensing module 76 or heart sound analyzer 80 detects, and transmit the marker codes to programmer 24. An example IMD with marker-channel capability is described in U.S. Pat. No. 4,374,382 (Markowitz), hereby incorporated herein by reference in its entirety. Information which processor 70 may transmit to programmer 24 via telemetry module 78 may also include indications of treatable rhythms, indications of EGM reliability and use of heart sound signals for detecting or confirming a tachyarrhythmia, and indications of non-treatable rhythms in which the EGM based analysis indicated that the rhythm was treatable and the heart sound analysis indicated that the rhythm was non-treatable. Such information may be included as part of a marker channel with an EGM.

Figure 4:
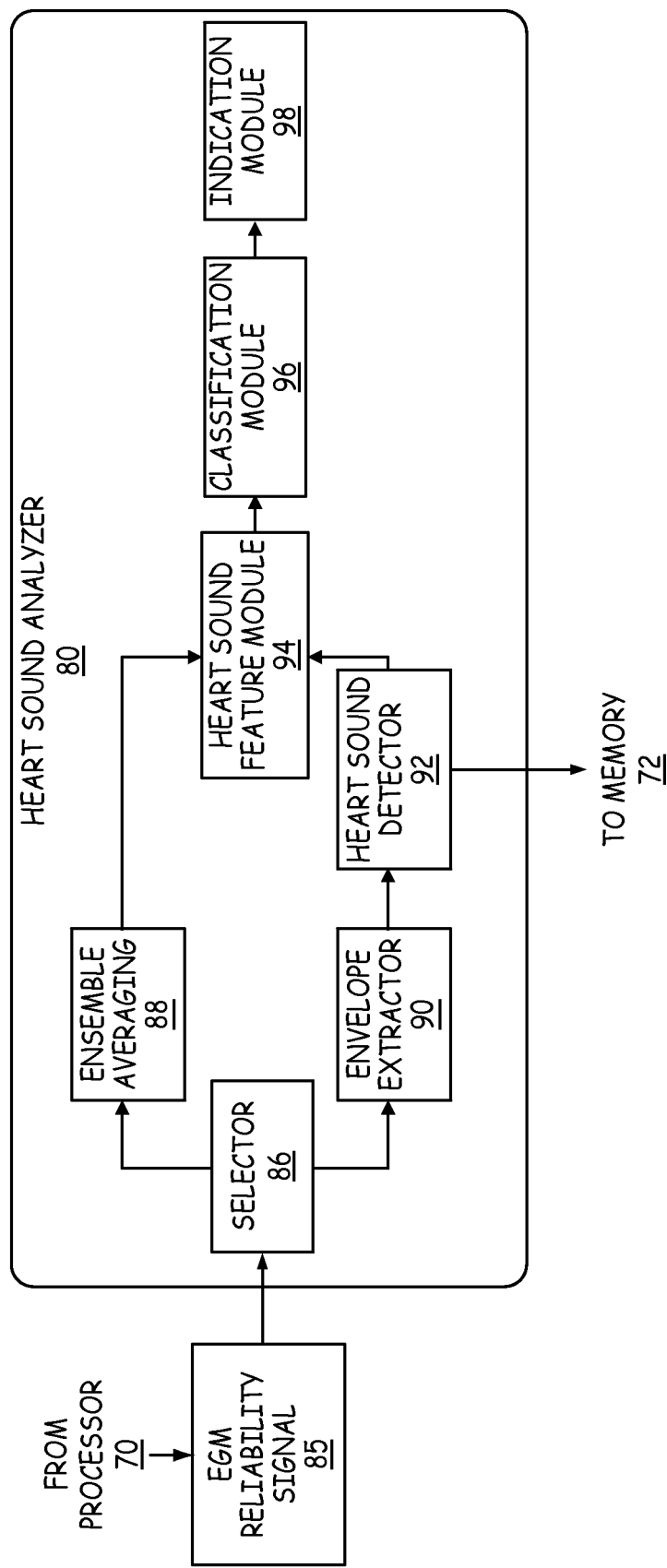
FIG. 4 is a block diagram illustrating an example configuration of the heart sound analysis module shown in FIG. 3.

FIG. 4 is a block diagram illustrating an example configuration of heart sound analyzer 80. As illustrated in FIG. 4, heart sound analyzer 80 may include a heart sound analysis selector 86 responsive to an EGM reliability signal 85 received from processor 70. The heart sound analyzer 80 may further include an ensemble averaging module 88, an envelope extractor 90, heart sound detector 92, heart sound feature module 94, classification module 96, and indication module 98.

In one embodiment, selector 86 enables one of ensemble averaging module 88 and envelope extractor 90 in response to the EGM reliability signal 85. Processor 70 determines if the EGM signal (or ECG in some embodiments) is reliable for rhythm determination. This determination may be made based on a signal-to-noise analysis, suspected oversensing or other EGM/ECG signal reliability or acceptability criteria. Example methods for detecting oversensing or noise corruption of a cardiac electrical activity signal that may be implemented in the techniques disclosed herein for determining EGM reliability are generally disclosed in U.S. Pat. No. 7,783,354 (Gunderson), U.S. Pat. No. 7,831,304 (Cao et al.), U.S. Pat. No. 7,904,153 (Greenhut, et al.), and U.S. Publication No. 2011/0186247 (Cao, et al), all of which references are hereby incorporated herein by reference in their entirety.

If the EGM signal is determined to be reliable for rhythm detection, heart sound analysis may be used to determine if an EGM-based ventricular tachyarrhythmia detection is stable or not. A stable rhythm is considered "non-treatable". If a heart sound signal indicates regular mechanical activity associated with the electrical activity and without significantly diminished hemodynamic function, a tachyarrhythmia therapy, particularly a shock therapy, is not necessary. On the other hand, if the heart sound signal indicates irregular mechanical activity dissociated with the electrical activity or significantly diminished hemodynamic function, it is desirable to treat the unstable rhythm. An unstable rhythm is considered "treatable".

If the EGM is reliable, ensemble averaging module 88 receives a signal from heart sound sensor 82 and is enabled to compute an ensemble average of the heart sound signal over an averaging interval selected from multiple cardiac cycles. The averaging interval is established during each cardiac cycle using the EGM signal. For example, the heart sound signal may be sampled over an averaging interval that begins upon an EGM sensed R-wave and ends a programmed time interval after the sensed R-wave, e.g. 400 ms. Thus, the heart sound signal analysis performed by heart sound analyzer 80 involving ensemble averaging is dependent on a reliable EGM signal for setting the averaging interval on a beat-by-beat basis (which may include consecutive or non-consecutive beats).

Ensemble averaging module 88 may sample the heart sound signal received from the sensor, e.g. at a sampling rate of 256 Hz, and filter the signal before performing ensemble averaging. Ensemble averaging module 88 may filter the heart sound signal, for example by bandpass filter having a passband of approximately 40 Hz to approximately 90 Hz, to attenuate respiration artifact or other non-cardiac signal artifact. The sampled and filtered signals obtained during the averaging interval over multiple cardiac cycles are then aligned and averaged to obtain an ensemble average of the heart sound signal.

The number of cardiac cycles used for computing the ensemble average may vary and may depend on the NID, signal-to-noise ratio of the heart sound signal, or other factors. The selector 86 may be configured to select the ensemble averaging method for analyzing heart sounds as well as set the averaging interval and number of cardiac cycles used by ensemble averaging module 88 based on information received from processor 70 and/or memory 72, such as a programmed NID, detected heart rate, or whether initial detection or redetection is taking place. Details regarding parameters controlling ensemble averaging will be described further in conjunction with FIGS. 7 and 8.

Ensemble averaging module 88 computes an ensemble average of the heart sound signal from which heart sound feature module 94 extracts features used to classify the averaged heart sound signal as normal or abnormal. The ensemble averaged signal may be used directly or additional processing may be performed by heart sound feature module 94 for extracting feature values. In some embodiments, the ensemble averaged signal may be smoothed and an envelope of the ensemble averaged signal may be determined from which the heart sound feature module 94 extracts heart sound features. Examples of heart sound ensemble averaged signals and envelope signals derived therefrom are presented in FIGS. 9 and 10.

If the EGM reliability signal 85 indicates that the EGM signal is unreliable for rhythm detection, the selector 86 enables envelope extractor 90 to extract an envelope of the heart sound signal independent of a cardiac electrical activity signal, i.e. independent of an EGM (or ECG) signal. If the EGM is unreliable due to noise, undersensing or oversensing, the EGM signal cannot be relied upon for establishing ensemble averaging windows. As such, if the EGM signal is unreliable, heart sound analyzer 80 is enabled to perform heart sound analysis independent of the EGM signal. Heart sound analyzer 80 and processor 70 may make a tachyarrhythmia detection and therapy decision independent of the EGM signal.

Envelope extractor 90 receives an electrical signal from heart sound sensor 82. The electrical signal may be digitized and parsed into segments of predetermined length. As an example, the electrical signal generated by heart sound sensor 82 may be sampled at a 256 Hertz (Hz) rate and parsed into segments including 100 or more sample points. Generally, envelope extractor 90 processes the received signal to extract an envelope, i.e., generate an envelope signal from the received signal.

In some examples, envelope extractor 90 band pass filters, rectifies, and smoothes the sensor signal before extracting the envelope signal. For example, envelope extractor 90 may include a high pass filter, e.g., a 40 Hz high pass filter, and a low pass filter, such as a 70 Hz low pass filter, to remove unwanted signal components from the heart sound sensor signal. In some examples a first order infinite impulse response (IIR) high pass filter with a cutoff frequency of 40 Hz and a third order IIR low pass filter with a cutoff frequency of 70 Hz may be used. In some examples, analog filtering of the heart sound sensor signal may additionally or alternatively be performed prior to digitization of the signal and receipt by envelope extractor 90. As discussed above, IMD 16 may include analog-to-digital conversion circuitry.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In other examples, envelope extractor 90 may use other methods to generate the envelope signal, such as the normalized Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to heart sound detector 92.

Heart sound detector 92 utilizes an algorithm to detect heart sounds within the envelope signal. Since the EGM signal is unavailable for parsing the heart sound envelope signal into cardiac cycles to differentiate the expected timing of particular heart sounds, such as S1, S2 etc., within the cardiac cycle, the heart sound detector 92 is configured to detect when heart sounds corresponding to cardiac cycle events are occurring. Generally, heart sound detector 92 identifies the local maximums of the envelope signal. In order to identify the local maximums that correspond to heart sounds, heart sound detector 92 may utilize an adaptively decaying threshold. The adaptively decaying threshold is determined based on the running average of detected heart sound amplitudes, the running average of the envelope signal amplitude, and the mean heart sound-to-heart sound interval. Heart sound detector 92 compares the envelope signal to the adaptively decaying threshold to identify the local maximums. Heart sound detector 92 may store markers, referred to as "heart sound markers," for the identified local maximums within memory 72 or provide the heart sound markers directly to heart sound feature module 94. An example algorithm for detecting heart sounds within an envelope signal is described in detail in the above-incorporated U.S. Publication No. 2010/0331903, incorporated herein by reference init's entirety.

Heart sound feature module 94 extracts features of the detected heart sounds (received from module 92) or from the ensemble averaged signal(s) (received from module 88). Heart sound feature module 94 may extract the same or different heart sounds from an ensemble averaged signal than from the envelope signal received from heart sound detector 92. The heart sound features extracted from the ensemble averaged signal are used primarily for indicating whether a tachyarrhythmia detected based on the reliable EGM signal is treatable or non-treatable rhythm. The heart sound features extracted from the heart sound detector signal may be used to detect a heart rate or a tachyarrhythmia independent of EGM signals when the EGM signal is unreliable and may additionally be used to establish if the heart rhythm is treatable or non-treatable.

As such, heart sound features extracted from the ensemble averaged signal may be primarily correlated to hemodynamic function or surrogates of a hemodynamic measure. An example of heart sound features that may be extracted from an ensemble averaged signal include the S1 amplitude. Additionally or alternatively, heart sound features extracted from the ensemble averaged signal may be used to determine whether the electrical activity and the mechanical activity of the heart is associated or dissociated based on time intervals measured between features of the EGM signal and features of the ensemble averaged signal. For example, a time interval from the beginning or end of the EGM-based averaging interval to a heart sound feature may be measured.

Heart sound features extracted from the heart sound detector signal 92 may be related to cardiac cycle intervals for determining the heart rate and may additionally be related to hemodynamic function for determining if a detected fast heart rate is hemodynamically stable. Example heart sound features that may be extracted from the envelope signal include the mean period ratio (MPR) and matching score (MS) for a detected heart sound. These features may be used to detect a heart rhythm and may additionally be used to determine if the rhythm is hemodynamically stable when the EGM signal is unreliable.

The MPR for a detected heart sound is the period of the detected heart sound divided by the mean period of one or more template heart sounds. The MS may be determined using template matching schemes that compare detected heart sounds to template heart sounds, such as a wavelet template matching scheme or a "bounded template" matching scheme. An example wavelet template matching scheme is disclosed in commonly-assigned U.S. Pat. No. 6,393,316 (Gillberg), hereby incorporated herein by reference in its entirety. An example bounded template matching scheme is disclosed in a commonly-assigned and co-pending U.S. Patent Publication No. 2010/0185109 (Zhang, et al.), hereby incorporated herein by reference in its entirety.

In some examples, template heart sounds used for determining the MPR and MS may be example heart sounds that are loaded into heart sound feature module 94. In other examples, template heart sounds may be heart sounds that were measured during a baseline interval of the patient. That is, the template heart sounds may be obtained from patient 14 during an identified or predetermined time period during which the patient is known to have a normal cardiac rhythm.

When receiving signals from heart sound detector 92, heart sound feature module 94 may use a heart sound marker from heart sound detector 92 to center a window, e.g., a 48 point or sample window, at a detected heart sound and use the resulting segment of samples to determine the MPR and MS. For example, heart sound feature module 94 may determine the period of the band-pass filtered signal segment and use it to determine the MPR, and may compare the extracted envelope signal segment to a stored template to determine the MS. Heart sound feature module 94 may then provide the MPR and MS to classification module 96.

When receiving an ensemble averaged signal from averaging module 88, heart sound feature module 94 may detect a signal feature by peak detection, area estimation, signal width measurement or other aspects of the averaged signal. The onset, end or midpoint of the averaging interval may be used as a reference point for searching for aspects of the averaged signal to be measured as heart sound features.

Classification module 96 classifies determined heart sound features as either normal or abnormal based on comparisons between the feature values and reference or threshold values. Classification of the heart sound features as normal or abnormal may be based on whether the features, e.g., the S1 amplitude, R-wave to S1 time interval, MPR or MS values, are within a predetermined range, or above or below a predetermined threshold. When heart sound analyzer 80 is operating in an EGM-dependent mode, i.e. ensemble averaging module 88 is enabled, classification module will classify the ensemble averaged signal, which may represent two or more cardiac cycles. When heart sound analyzer 80 is operating in an EGM-independent mode, i.e. when envelope extractor 90 and heart sound detector 92 are enabled, classification module 96 classifies each detected heart sound individually.

Indication module 98 receives the classification information for the heart sound features from classification module 96, and generates an indication whether the cardiac rhythm is treatable or non-treatable, e.g., whether to deliver or withhold a therapy scheduled to terminate a tachyarrhythmia, based on the received information. Indication module 98 may generate the indication based on one or more heart sound features obtained from a single ensemble averaged signal or multiple ensemble averaged signals when the EGM signal is reliable. Indication module 98 may generate the indication based on normal or abnormal classification of one or more heart sounds obtained from heart sound detector 92.

As an example, indication module 98 may generate an indication that a rhythm detected as a tachyarrhythmia based on EGM analysis is treatable when a feature of the ensemble averaged signal presents greater than a threshold percentage change from a baseline ensemble averaged signal feature value. Indication module 98 generates an indication that the rhythm is non-treatable when a feature of the ensemble averaged signal presents less than a threshold change from the baseline value. Separation of treatable from non-treatable rhythms may be defined by a single threshold or two different thresholds, i.e. an abnormal threshold and a normal threshold.

In some cases, classification module may classify a feature value difference as "intermediate" when the difference falls between two thresholds defining treatable and non-treatable rhythms. For example, the feature value difference between an ensemble averaged signal and a baseline value may be intermediate a "normal" threshold and an "abnormal" threshold. In this case, indication module may give an indication of an "intermediate" rhythm status. The processor may then make a therapy delivery or therapy scheduling decision based on this information in addition to EGM signal information. The decision may be to immediately deliver therapy based on a severity of the EGM signal-based rhythm detection or withhold or delay a therapy pending additional analysis of the EGM and/or heart sound signals.

When classification module 96 provides indication module 98 the classifications of individual heart sounds detected by heart sound detector 92, indication module 98 may generate an indication of a treatable or non-treatable rhythm based on a threshold number of heart sounds being classified as abnormal or normal. For example, if a threshold number of consecutive or proximate heart sounds, e.g., six of the last eight heart sounds or M out of N heart sounds, are classified as normal, indication module 98 generates an indication that a rhythm is non-treatable. In other examples, the threshold number may be a threshold number of abnormal heart sounds. In still other examples, classification module 96 may classify heart beats as normal or abnormal based on the classification of one or more heart sounds within each of the beats, and indication module may provide the indication as described based on a threshold number of normal or abnormal heart beats. Indication module 98 provides an indication to processor 70, which selectively delivers therapy based on the heart sound based indication received from indication module 98. This decision may be made independent of the EGM signal when the EGM signal is determined to be unreliable.

Figure 5:
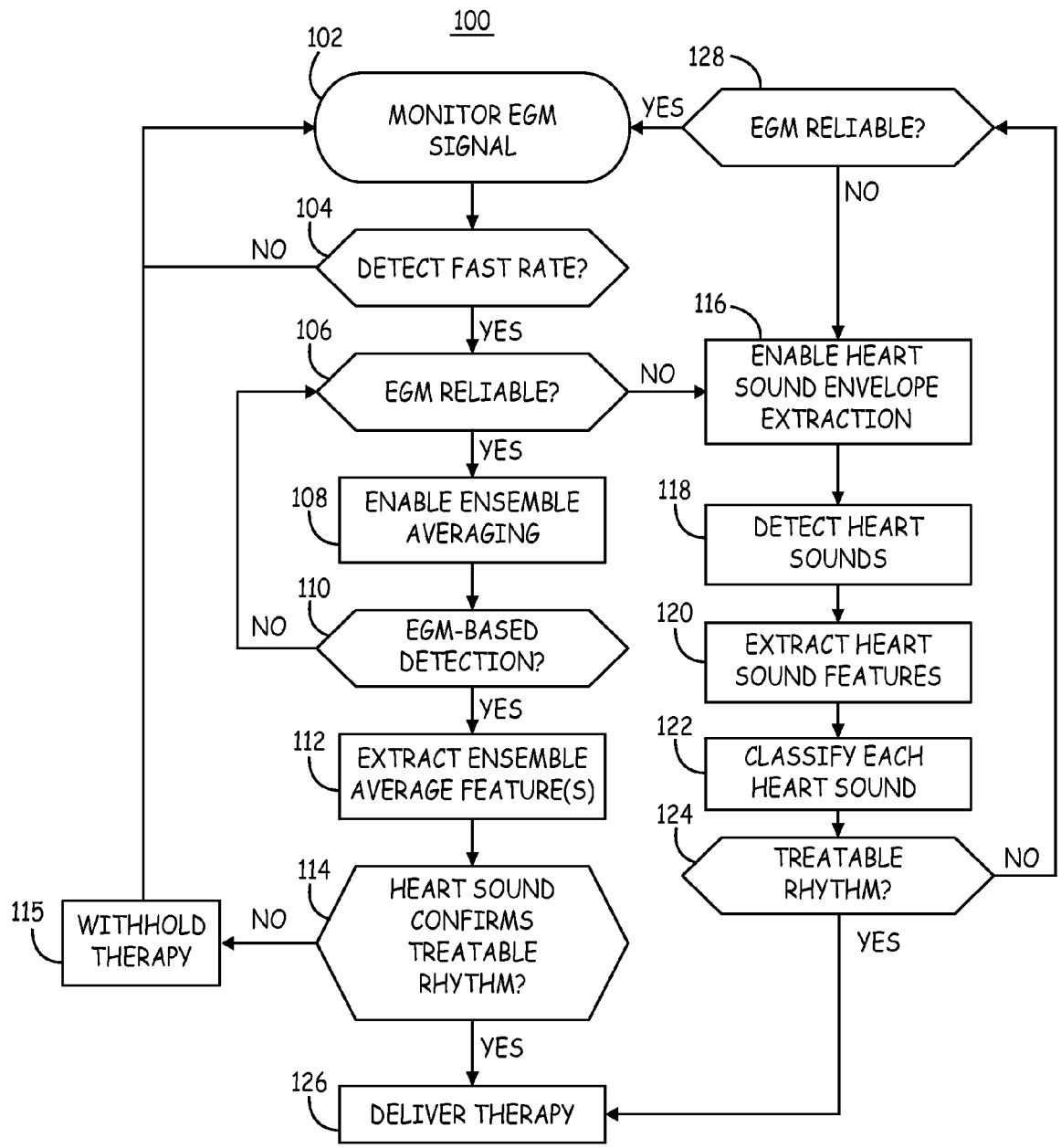
FIG. 5 is a flow diagram illustrating an example method for allowing or withholding a tachyarrhythmia therapy based on heart sound sensing.

FIG. 5 is a flow diagram 100 illustrating an example method for allowing or withholding a tachyarrhythmia therapy based on heart sound sensing. The example method is described with respect to IMD 16 and its components shown in FIG. 3, but in other examples may be practiced, at least in part, by another device, such as programmer 24.

Flow chart 100 and other flow charts presented herein are intended to illustrate the functional operation of the device, and should not be construed as reflective of a specific form of software, firmware, or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern medical device system, given the disclosure herein, is within the abilities of one of skill in the art.

Methods described in conjunction with flow charts presented herein may be implemented in a non-transitory computer-readable medium that includes instructions for causing a programmable processor to carry out the methods described. The instructions may be implemented as one or more software modules, which may be executed by themselves or in combination with other software.

According to the illustrated example, processor 70 monitors an EGM signal at block 102. More generally, a cardiac electrical activity signal is monitored which could be an EGM signal or an ECG signal. If the processor detects a fast rate (block 104) based on measured intervals between cardiac electrical events, e.g. R-waves, the electrical signal is analyzed for reliability at block 106. In some embodiments, a fast rate detected at block 104 may be a sensed heart rate above a detection rate that has not yet reached a required NID. For example a fast rate may be detected based on 3 consecutive beats shorter than a tachyarrhythmia detection interval or other criteria indicating a "concerning" rhythm state that does not yet meet VT or VF detection criteria. In other embodiments, a fast rate detection at block 104 may be detection of an SVT, VT or VF based on EGM interval-based or morphology based analysis.

EGM reliability analysis may include diagnostic algorithms for detecting lead-related noise, e.g. lead fracture or dislodgment, T-wave over sensing, EMI oversensing, or signal-to-noise ratio analysis. In some examples, EGM reliability monitoring may be performed continuously or periodically and whenever the EGM is deemed unreliable for rhythm detection, heart sound analyzer 80 enables envelope extractor at block 116 for detecting heart sounds and utilizing heart sound signals for rhythm detection and therapy decisions. In other examples, EGM reliability may be determined only after a concerning rhythm or tachyarrhythmia is already detected based on the EGM signal. If the EGM is unreliable, heart sound envelope extractor is enabled at block 116.

In response to a reliable EGM signal indication at block 106, the ensemble averaging module 88 is enabled at block 108 and computes an ensemble average of the heart sound signal sampled over the averaging interval for a selected number of cardiac cycles. In one embodiment, the number of cardiac cycles corresponds to a programmed NID. If an EGM analysis results in a tachyarrhythmia detection at block 110, heart sound features are extracted from the ensemble averaged signal at block 112. At block 114, the heart sound feature(s) for the ensemble averaged signal are compared to respective threshold or baseline values. In one embodiment the S1 amplitude is determined from the ensemble averaged signal and compared to a previously determined normal sinus rhythm (NSR) S1 amplitude. If the S1 amplitude is less than a predetermined percentage of the baseline value, the heart sound analysis confirms an unstable or treatable rhythm at block 114. Heart sound analyzer 80 provides an indication that the rhythm is treatable to processor 70. Processor 70 controls signal generator 74 to deliver a programmed therapy, e.g., a cardioversion or defibrillation shock, at block 126.

If a heart sound feature measured from the ensemble averaged signal substantially matches a baseline NSR heart sound feature value, an indication of a non-treatable rhythm is provided. For example, if the S1 amplitude (or other heart sound feature measured from the ensemble averaged signal) is greater than a predetermined percentage of the baseline NSR S1 amplitude, heart sound analyzer 80 provides an indication that the rhythm is non-treatable. Processor 70 withholds the therapy at block 115, e.g., does not control signal generator 74 to deliver the scheduled therapy. Processor 70 and analyzer 80 may then continue to monitor the EGM and heart sound signals, respectively (return to block 102).

In response to a signal from processor 70 indicating the EGM is unreliable for rhythm detection, heart sound analyzer 80 is enabled to receive a raw signal from heart sound sensor 82. Heart sound analyzer 80 may analyze the heart sound signal substantially continuously. At block 116, heart sound envelope extractor 90 extracts the envelope signal of the sampled heart sound signal.

Envelope extractor 90 rectifies the filtered signal and smoothes the filtered signal to obtain an envelope signal from the filtered signal. In one example, envelope extractor 90 may smooth the filtered signal by summing together and averaging a left-shifted version of the signal, the initial signal, and a right-shifted version of the signal. Envelope extractor 90 may apply a boxcar filter to the resulting signal to extract the envelope signal. Generally, the number of points used in the boxcar filter may be dependent on the sampling rate. As one example, the boxcar filter may be a 16 point boxcar filter when the sample rate is approximately 256 Hz.

Other filters or signal processing techniques may be used to extract the envelope signal. In some examples, wavelet transforms may be used instead of or in addition to the bandpass filtering. Wavelet transforms may also allow automatic identification of the wavelet levels which contain heart sound information.

Heart sound detector 92 detects the occurrence of heart sounds in the envelope signal at block 118. Heart sound detector detects the heart sounds independent of the EGM signal, which has been indicated as being unreliable. Generally, heart sound detector 92 identifies the local maximums of the envelope signal and may utilize an adaptively decaying threshold.

At block 120, heart sound feature module 94 determines one or more heart sound features from each of the detected heart sounds based on the envelope signal and/or the filtered heart sound signal. Classification module 96 classifies each of the detected heart sounds as either normal or abnormal based on the heart sound features at block 122. As an example, classification module 96 may compare heart sound feature values of a detected heart sound to a predetermined range of values. When the heart sound feature value(s) of the detected heart sound are within the predetermined range of values, classification module 96 may classify the detected heart sound as normal. However, if a heart sound feature value of the detected heart sound is not within the predetermined range of values, the detected heart sound may be classified as abnormal.

At block 124, indication module 98 provides an indication to processor 70 of whether the heart rhythm is treatable or non-treatable based on the classification of one or more of the heart sounds. For example, indication module 98 may indicate that the heart rhythm is non-treatable when at least M of the last N heart sounds are classified as normal. Processor 70 allows or withholds a therapy based on the classification of the heart sounds, e.g., based on the indication from indication module 98. If the indication is "non-treatable", the process advances to block 128 to determine if the EGM signal is still unreliable, and if so, heart sound analysis continues using heart sound envelope extraction and heart sound detection at blocks 116 and 118. If the indication is "treatable", a therapy is delivered at block 126.

The process shown by the flow diagram 100, which may generally be performed by heart sound analyzer 80 and processor 70, utilizes the EGM signal (or more generally cardiac electrical activity signal) when the EGM signal is identified as being reliable for computing an ensemble averaged heart sound signal over multiple cardiac cycles. A single set, i.e. one or more, heart sound features are derived from the ensemble averaged heart sound signal that represents the heart sound signal occurring over the multiple cardiac cycles. The single set of heart sound features from one ensemble averaged signal may be used to provide an indication of a treatable or a non-treatable rhythm. In contrast, when the EGM signal is identified as being unreliable, a set of (i.e. one or more) heart sounds is determined for each of the detected heart sounds individually so that each individually detected heart sound can be classified as abnormal or normal. Based on a count of the individually classified heart sounds, the heart sound analyzer provides an indication of a treatable or non-treatable rhythm. In other words, in the EGM-independent method, the heart sound features are determined on a beat-by-beat basis for classifying each beat whereas in the EGM-dependent method, heart sound features are determined from an ensemble average representing a group of beats.

Figure 6:
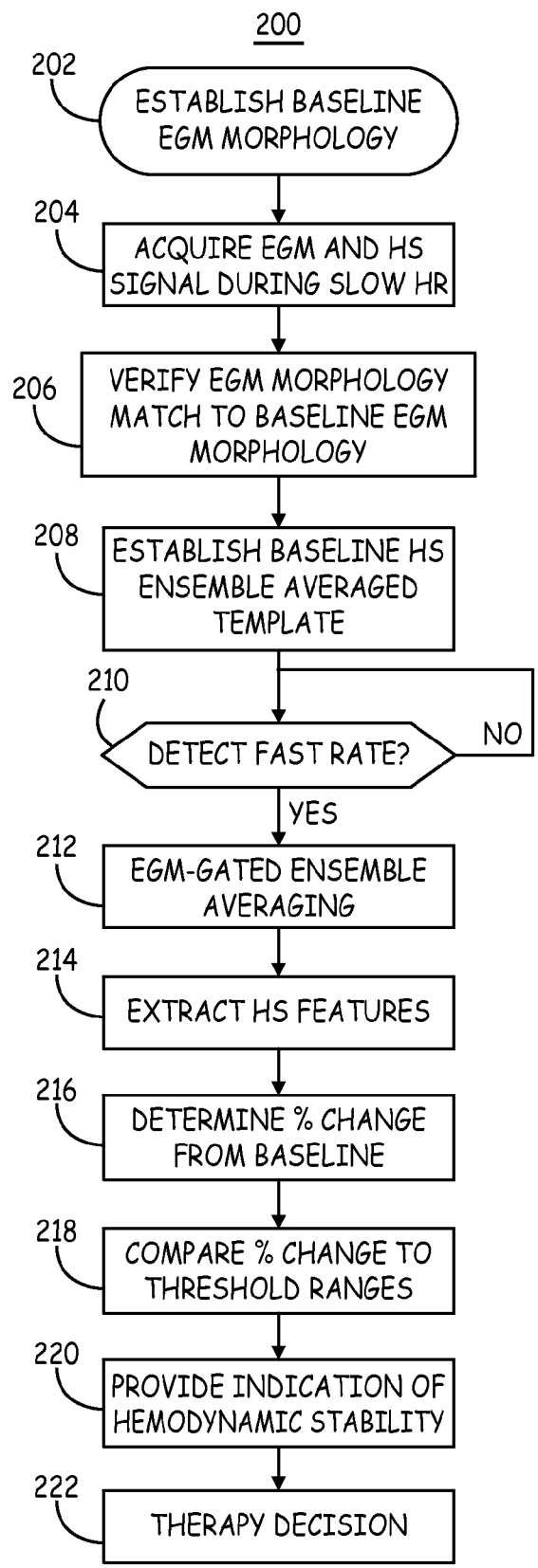
FIG. 6 is a flow diagram illustrating an example method for establishing a baseline ensemble averaged heart sound signal and using the baseline signal for providing an indication of rhythm stability.

FIG. 6 is a flow diagram 200 illustrating an example method for establishing a baseline ensemble averaged heart sound signal and using the baseline signal for providing an indication of rhythm stability. The example method is described with respect to heart sound analyzer 80 and its components, and processor 70, but it should be understood that the example method may be performed by any one or more devices, processors, or components described herein.

At block 202, a baseline EGM morphology signal, e.g. a QRS signal morphology, is established by processor 70 using a digitized EGM signal from sensing module 76. The baseline EGM morphology signal is established during a confirmed normal sinus rhythm, for example under the supervision of a clinician. At block 204, the EGM signal and a heart sound signal are acquired during a slow heart rate (HR). A slow heart rate may be defined by a sustained series of R-R intervals longer than a tachyarrhythmia detection threshold or lower than a "concerning" rhythm threshold or normal HR upper limit (e.g., 90 bpm). During the slow heart rate, the EGM signal morphology is compared to the baseline EGM morphology to confirm NSR. Verification of NSR using EGM intervals and morphology may be done automatically by the IMD on a periodic basis or any time a low heart rate is sensed for enabling the establishing or updating of a baseline heart sound template.

Once a slow heart rate and NSR EGM signal morphology are verified (blocks 204 and 206), a baseline ensemble average of the heart sound signal is established at block 208. A feature or event of the EGM signal, such as a sensed R-wave, is used to set an ensemble averaging interval for each of multiple cardiac cycles. The heart sound signal is sampled and stored during each of the averaging intervals. The heart sound signals are then aligned based on the EGM-referenced averaging interval, and the signals are averaged together. Heart sound signal feature values may then be determined from the baseline ensemble averaged template for use as baseline or reference values during tachyarrhythmia detection and therapy decision-making. Additional details regarding establishing a baseline heart sound ensemble average will be described in conjunction with FIG. 7.

After establishing the baseline ensemble average heart sound signal, the EGM signal is monitored at block 210 until a fast rate is detected, i.e. RR intervals shorter than a tachyarrhythmia detection interval. As described previously in conjunction with FIG. 5, in some embodiments the EGM reliability is verified upon detecting a concerning rhythm (e.g. a rate that includes RR intervals shorter than a detection threshold but not yet satisfying NID criterion) before enabling the ensemble averaging module 88. If a fast rate is detected at block 210 and the EGM is deemed reliable, the heart sound analyzer 80 enables ensemble averaging module 88 to determine a heart sound ensemble averaged signal at block 212 during the fast rate using the EGM signal to set averaging intervals and as a time reference for aligning heart sound signals in the same manner as used for establishing the baseline heart sound signal.

At block 214, heart sound features are extracted from the ensemble averaged signal. In one example, the S1 amplitude is extracted. In another example a time interval between an R-wave sense (which may correspond to the beginning of the averaging interval) and subsequent S1 peak is measured. As such, heart sound features extracted from an ensemble averaged signal may include features of the heart sound signal, time intervals measured between features of the heart sound signal, and time intervals between features of the EGM signal or EGM-based averaging interval and the heart sound signal.

At block 216, a percentage change or difference from the baseline ensemble averaged heart sound signal features established at block 208 is determined. For example, a percentage change may be determined as the difference between the feature value from the ensemble averaged signal during the fast rate and the corresponding feature value from the baseline ensemble averaged signal divided by the baseline feature value.

The percentage change in the heart sound feature value during the fast rate compared to the baseline value is compared to threshold ranges defined for discriminating between a stable rhythm and an unstable rhythm at block 218. In response to the comparison, an indication of hemodynamic stability is provided at block 220. In one embodiment, if the percentage change is large, e.g. represents more than approximately 80 to 90% change in the feature value, the indication module 98 of heart sound analyzer 80 provides an indication of an unstable or treatable rhythm at block 220. This information may be used by processor 70 to detect a treatable rhythm based on both the EGM and heart sound signals and make a therapy delivery decision at block 222 to deliver a therapy, for example to deliver a cardioversion or defibrillation shock.

If the percentage change is small, e.g. represents less than approximately 10% to 20% change from the baseline feature value, the indication module 96 provides an indication of a stable rhythm at block 220. The processor 70 may use this information to detect a non-treatable rhythm. The processor 70 may make a therapy decision at block 222 that includes withholding a shock therapy. The therapy decision may further include delivering an anti-tachycardia therapy to preempt deterioration to a hemodynamically unstable rhythm or to withhold all types of therapies.

In some embodiments, the change in the heart sound feature value may be intermediate to a threshold indicating a treatable rhythm and a threshold indicating a non-treatable rhythm. For example, if the change represents a decrease that falls between the two thresholds discriminating treatable and non-treatable rhythms, the indication module 98 may provide an intermediate indication. The processor 70 may use this intermediate indication in making therapy decisions at block 222. For example, based on any combination of the indicated intermediate status, EGM-measured intervals, and EGM morphology analysis, the processor may determine an overall severity of the rhythm and select to deliver a shock therapy, withhold a shock therapy, deliver an anti-tachycardia pacing therapy, or post-pone a therapy to allow the rhythm to selfterminate and/or allow analysis of additional cardiac cycles of EGM and/or heart sound signal data or other physiological sensor signal data.

In other embodiments, a single threshold boundary may be defined for discriminating between hemodynamically stable and unstable rhythms. For example, if more than a 30% change (or other percentage change) in an ensemble averaged heart sound signal feature is detected, the rhythm may be indicated as being treatable.

Figure 7:
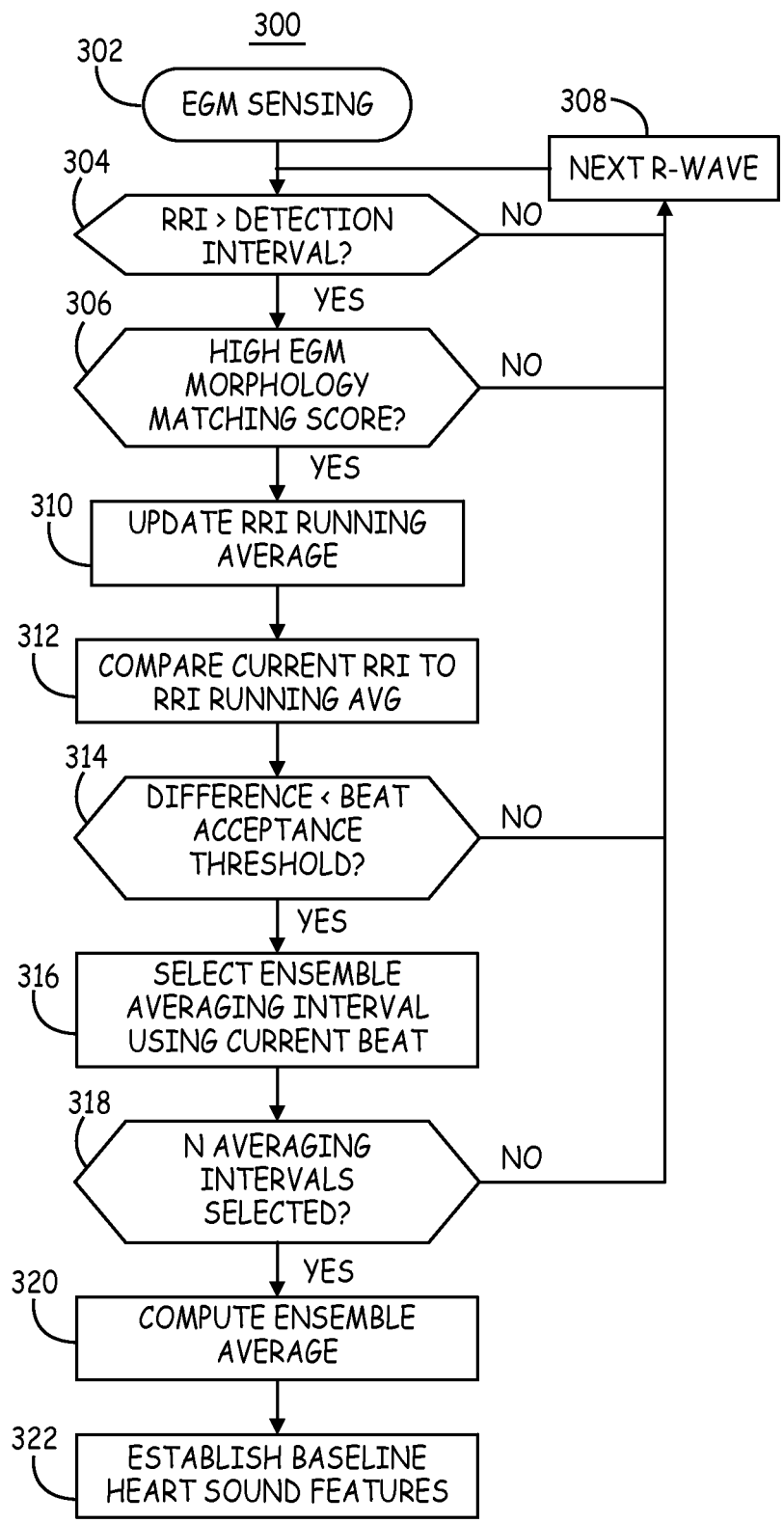
FIG. 7 is a flow chart of a method for computing an ensemble averaged heart sound signal according to one embodiment.

FIG. 7 is a flow chart 300 of a method for computing an ensemble averaged heart sound signal according to one embodiment. The EGM signal sensing is performed at block 302 for sensing R-waves and measuring RR intervals (RRIs). If the RRI is shorter than a tachyarrhythmia detection interval as determined at block 304, the RRI is not used for ensemble averaging to obtain a baseline heart sound signal template or feature value. The process advances to the next R-wave at block 308.

If the current RRI is longer than a tachyarrhythmia detection interval (block 304), the EGM signal morphology for the R-waves defining the RR interval is examined at block 306. A morphology matching score based on a wavelet analysis or other morphology analysis technique may be computed to determine a correlation score between the EGM signal morphology and a previously established NSR EGM signal template. If the EGM signal presents a high morphology matching score with the NSR template, the current RRI is used to update a running average of the RRI at block 310. In one embodiment, a running average of the RRI is computed over four cardiac cycles though the running average may be computed using more or fewer RRIs.

The current RRI is then compared to the RRI running average at block 312. If the difference between the current RRI and the RRI running average is less than an acceptance threshold, as determined at block 314, the current RRI will be selected for use by the ensemble averaging module for inclusion in computing an ensemble average of the heart sound signal at block 316. If the difference between the current RRI and the running average is greater than a beat acceptance threshold, the current RRI is rejected for use in computing a heart sound ensemble average. The process advances to block 308 to evaluate the next R-wave and next RRI.

At block 316, an averaging interval is selected from the accepted RRI by identifying a fiducial point of the EGM signal, e.g. the point at which an R-wave is sensed or an R-wave peak. The averaging interval is defined relative to the fiducial point, and the heart sound signal is sampled during the averaging interval. In one embodiment, an averaging interval is selected as an interval beginning from an R-wave sense and extending a defined interval, e.g. 250 to 400 ms, thereafter. Any interval of time may be defined relative to any fiducial point or a combination of fiducial points identified from the leading or trailing R-wave defining the RRI.

If a required number (N) of averaging intervals have been selected from qualified RRIs, as determined at block 318, the heart sound signals sampled over the N averaging intervals are aligned and averaged at block 320 to compute the heart sound ensemble average. From the ensemble average, baseline heart sound features are computed at block 322 and stored in IMD memory for use in comparing to heart sound features measured during a suspected tachyarrhythmia for use in indicating the stability of the heart rhythm. The required number of averaging intervals used for computing an ensemble average may vary between embodiments and may range from 2 to 12 intervals for example. The number of averaging intervals may depend on the signal to noise ratio of the heart sound signal, NID or other factors.

Figure 8:
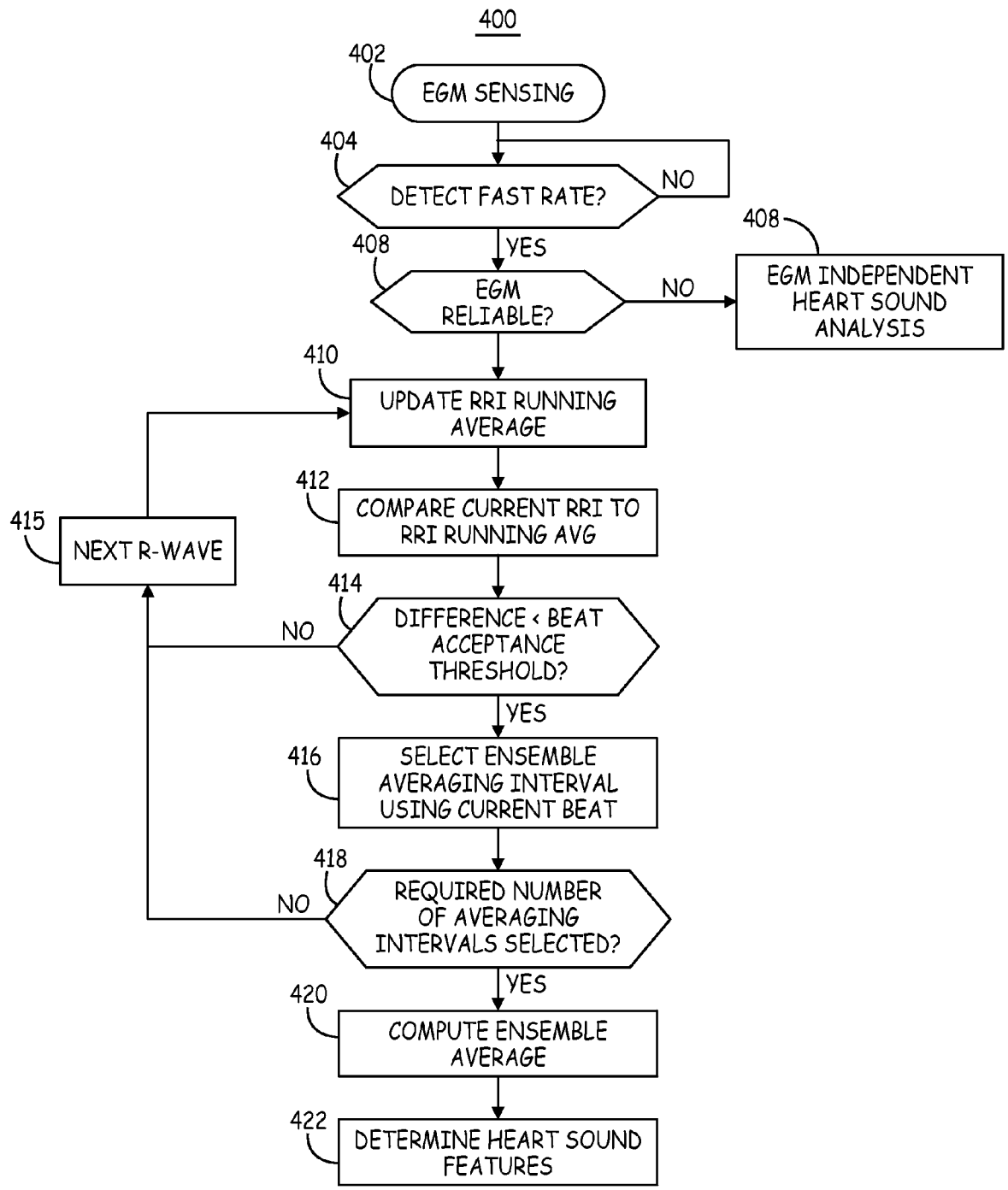
FIG. 8 is a flow chart of a method for determining ensemble averaged heart sound signal features for use in classifying a heart rhythm according to one embodiment.

FIG. 8 is a flow chart 400 of a method for determining ensemble averaged heart sound signal features for use in classifying a heart rhythm according to one embodiment. At block 402, EGM signal sensing is enabled and if a fast rate is detected based on EGM interval analysis (block 404), the EGM signal is evaluated for signal reliability at block 406. If the EGM signal is determined to be unreliable, EGM-independent heart sound analysis is enabled at block 408 as described previously. The heart sound signal is sampled continuously and a heart sound signal envelope is extracted from which heart sounds are detected and used for indicating a treatable or non-treatable rhythm as described above.

If the EGM signal is deemed reliable, the RRI running average is updated at block 410. In some embodiments, after detecting a fast rate, the RRI running average is updated on each beat without EGM morphology evaluation of the associated QRS signals for rejecting or accepting each RRI. The current RRI is compared to the running average RRI at block 412. If the difference between the current RRI and the running average is greater than a beat acceptance threshold (block 414), the current RRI is not used for selecting an ensemble averaging interval. The process advances to the next R-wave at block 415.

If the current RRI meets acceptability criterion, the ensemble averaging interval is selected from the current RRI at block 416. The averaging interval is based on a fiducial EGM signal point as a time interval reference point in the same manner as the selected averaging intervals used to establish a baseline ensemble averaged signal.

If a required number of averaging intervals has been selected (block 418), the ensemble average is computed at block 420. Otherwise, the process advances to the next sensed R-wave at block 415 to measure the next RRI. Once enough averaging intervals have been selected, the heart sound signals sampled over each averaging interval are aligned and averaged to compute the ensemble average. The required number of averaging intervals may be equal to or a proportion of the NID corresponding to the detected RRIs. In other embodiments, the required number may be based on a measured signal-to-noise ratio of the heart sound signal.

At block 422, one or more heart sound features are determined from the ensemble averaged signal. These heart sound features are compared to the analogous baseline heart sound feature values for providing an indication of the stability of the heart rhythm. This indication of a treatable or non-treatable rhythm is used by processor 70 for making therapy delivery decisions as described above.

Figure 9:
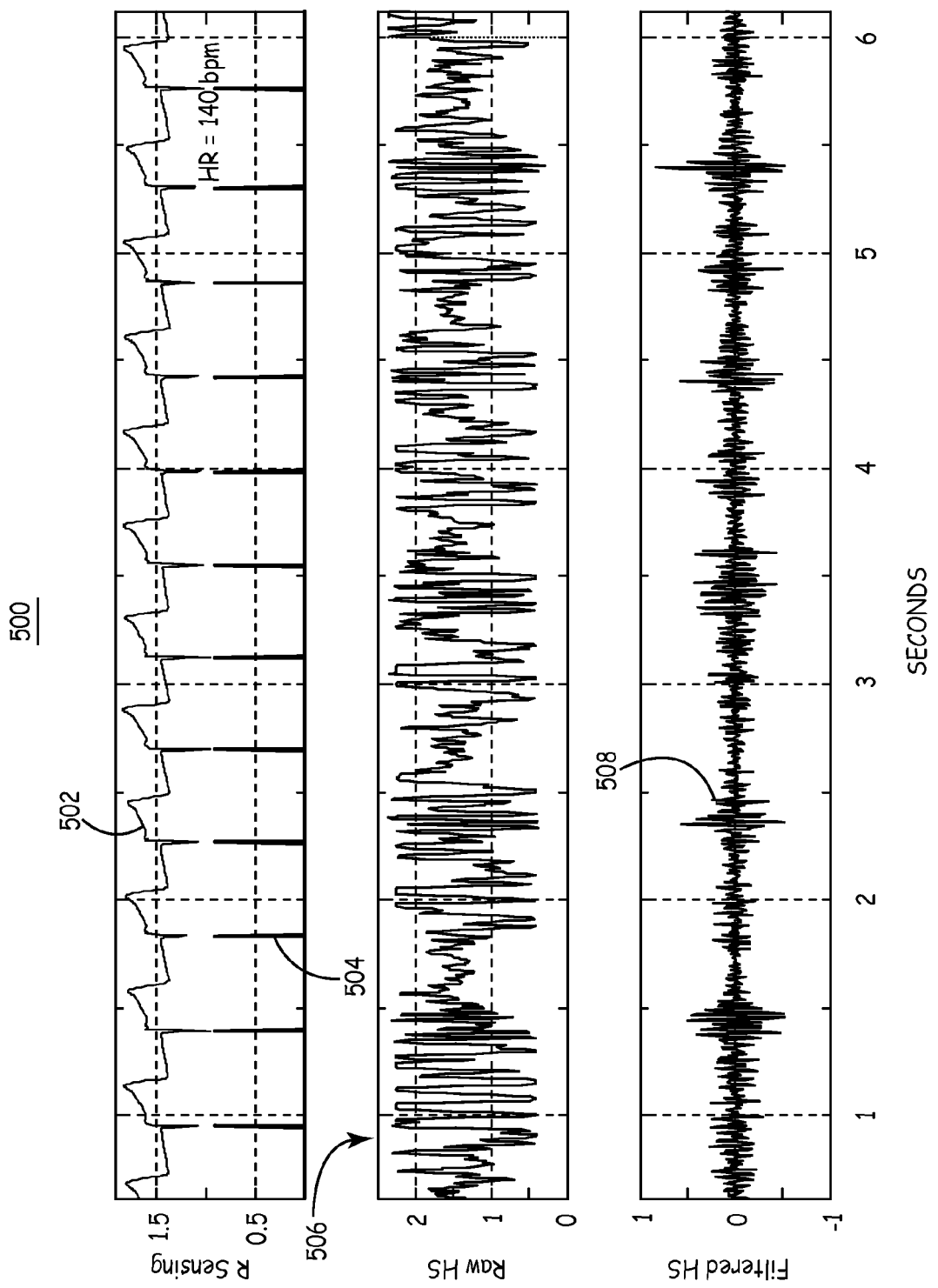
FIG. 9 is an example signal recording of an EGM signal, raw heart sound signal, and filtered heart sound signal.

FIG. 9 is an example recording 500 of an EGM signal 502, raw heart sound signal 506, and filtered heart sound signal 508. In particular EGM signal 502 is used for sensing cardiac electrical events, such as R-waves 504. EGM signal 502 in this example is a reliable EGM signal. Sensed R-waves 504 may be used in setting an ensemble averaging interval for averaging heart sound signals.

Raw heart sound signal 506 is the signal generated by a heart sound sensor and represents a signal that may be received by heart sound analyzer 80. Signal 508 represents a band pass filtered version of raw signal 506. Filtered signal 508 may be further processed by heart sound analyzer 80 for determining heart sound feature values. In particular, filtered signal 508 is used for determining an ensemble averaged signal.

Figure 10:
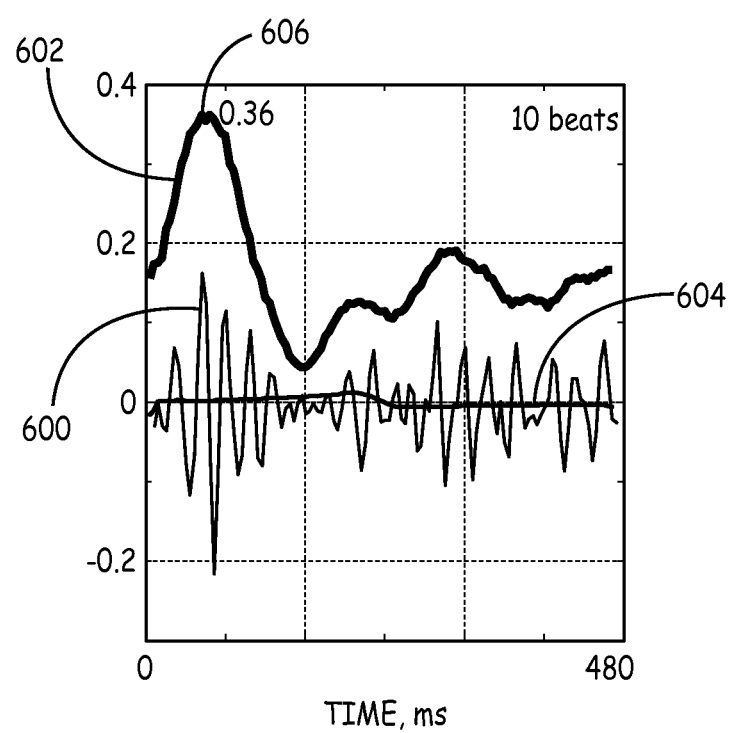
FIG. 10 is a depiction of an ensemble averaged heart sound signal determined from the filtered signal shown in FIG. 9.

FIG. 10 is a depiction of an ensemble averaged heart sound signal 600 determined from the filtered signal 508 shown in FIG. 9. The time of 0 ms corresponds to the occurrence of an R-wave sense (not shown in FIG. 10) of EGM signal 604. The ensemble averaged heart sound signal 600 is obtained by averaging the filtered signal 508 over 10 cardiac cycles in this example, beginning from the R-wave sense in each cycle and extending to 480 ms. The ensemble averaged signal 600 may be used directly for determining heart sound signal features or may be further processed by heart sound analyzer 80. For example, the ensemble averaged signal 600 may be rectified and smoothed to obtain the heart sound signal envelope 602. The heart sound signal features derived by heart sound feature module 94 may be determined from the ensemble averaged envelope signal 602. In one embodiment, the S1 peak amplitude 606, shown here as having a magnitude of 0.36 mV, is determined from the ensemble averaged envelope signal 602. While a particular averaging interval of 480 ms is used over 10 cardiac cycles in the example of FIG. 10, it is recognized that any desired averaging interval and number of cardiac cycles may be used for enabling reliable determination of selected heart sound features used in the rhythm analysis.

Thus, a medical device system and associated methods have been presented in the foregoing description with reference to specific embodiments for using heart sound signals in discriminating between treatable and non-treatable cardiac rhythms and making therapy delivery decisions. It is appreciated that various modifications to the referenced embodiments may be made without departing from the scope of the disclosure as set forth in the following claims. For example, any of the techniques or processes described in conjunction with block diagrams and flow charts presented herein may be combined or functional blocks may be omitted or re-ordered in alternative embodiments. The description of the embodiments is illustrative in nature and, thus, variations that do not depart from the gist of the disclosure are intended to be within the scope of the disclosure.

The invention claimed is:

1. A method for detecting cardiac events in a medical device, comprising:
    sensing cardiac electrical signals representative of electrical activity of a heart of a patient;
    detecting the cardiac event in response to the sensed cardiac signals;
    determining an indication of signal reliability corresponding to the sensed cardiac signals as being one of a reliable signal and a not reliable signal;
    switching operation of the device between a first mode of determining whether the sensed signal is one of treatable and not treatable and a second mode of determining whether the sensed signal is one of treatable and not treatable in response to the determined indication of signal reliability;
    sensing heart sounds and generating heart sounds signals representative of the sensed heart sound signals; and
    switching to the first mode in response to the indication of signal reliability corresponding to the sensed signal being a reliable signal, wherein the first mode comprises determining an ensemble averaged heart sound signal dependent on the cardiac electrical signal.

2. The method of claim 1, further comprising switching to the second mode in response to the indication of signal reliability corresponding to the sensed signal being a not reliable signal, wherein the second mode comprises detecting a plurality of heart sounds from the heart sound signal independent of the cardiac electrical signal.

3. The method of claim 2, wherein detecting the cardiac event comprises detecting whether a heart rate is greater than a detection threshold for a predetermined number of detection intervals less than a number of intervals to detect a treatable cardiac event.

4. The method of claim 2, further comprising:
    detecting a plurality of heart sounds within the heart sound signal;
    determining a feature of each of the detected heart sounds of the plurality of heart sounds;
    classifying each of the detected heart sounds as one of normal and abnormal; and
    generating an indication of a treatable rhythm in response to classifying at least M of a last N detected heart sounds as abnormal.

5. The method of claim 1, wherein determining the ensemble averaged heart sound signal comprises selecting an ensemble averaging interval in response to the cardiac electrical signal.

6. The method of claim 1, further comprising:
    determining a feature of the cardiac electrical signal corresponding to a cardiac cycle in response to an indication that the cardiac electrical signal is reliable; and
    determining whether to accept the cardiac cycle for inclusion in the ensemble averaged heart sound signal in response to the determined feature.

7. The method of claim 6, further comprising:
    determining a running average of a plurality of RR intervals;
    comparing the running average to the current RR interval; and
    accepting the cardiac cycle in response to a difference between the running average and the current RR interval being less than an acceptability threshold.

8. The method of claim 1, further comprising:
    determining a number of averaging intervals to be included in the ensemble averaged signal in response to an indication that the cardiac electrical signal is reliable, the number of averaging intervals corresponding to a required number of RR intervals to detect a tachyarrhythmia;
    determining the ensemble averaged signal in response to the determined number of averaging intervals;
    comparing the heart sound feature determined from the ensemble averaged signal to a previously established baseline heart sound feature value; and
    generating an indication of a treatable rhythm in response to the heart sound feature determined from the ensemble averaged signal representing greater than a threshold percentage change from the established baseline heart sound feature value.

9. A method for detecting cardiac events in a medical device, comprising:
    sensing cardiac electrical signals representative of electrical activity of a heart of a patient;
    detecting the cardiac event in response to the sensed cardiac signals;
    determining an indication of signal reliability corresponding to the sensed cardiac signals as being one of a reliable signal and a not reliable signal;
    switching operation of the device between a first mode of determining whether the sensed signal is one of treatable and not treatable and a second mode of determining whether the sensed signal is one of treatable and not treatable in response to the determined indication of signal reliability;
    sensing heart sounds and generating heart sounds signals representative of the sensed heart sound signals; and
    switching to the second mode in response to the indication of signal reliability corresponding to the sensed signal being a not reliable signal, wherein the second mode comprises detecting a plurality of heart sounds from the heart sound signal independent of the cardiac electrical signal.

10. A method for detecting cardiac events in a medical device, comprising:
sensing cardiac electrical signals representative of electrical activity of a heart of a patient;
detecting the cardiac event in response to the sensed cardiac signals;
determining an indication of signal reliability corresponding to the sensed cardiac signals as being one of a reliable signal and a not reliable signal; and
switching operation of the device between a first mode of determining whether the sensed signal is one of treatable and not treatable and a second mode of determining whether the sensed signal is one of treatable and not treatable in response to the determined indication of signal reliability, wherein detecting the cardiac event comprises detecting whether a heart rate is greater than a detection threshold for a predetermined number of detection intervals less than a number of intervals to detect a treatable cardiac event.

11. A medical device for detecting cardiac events, comprising:
a plurality of electrodes to sense cardiac electrical signals representative of electrical activity of a heart of a patient;
a processor configured to detect a cardiac event in response to the sensed cardiac signals, determine an indication of signal reliability corresponding to the sensed cardiac signals as being one of a reliable signal and a not reliable signal, and switch operation between a first mode of determining whether the sensed signal is one of treatable and not treatable and a second mode of determining whether the sensed signal is one of treatable and not treatable in response to the determined indication of signal reliability; and
a heart sound sensor to sense heart sounds and generate heart sounds signals representative of the sensed heart sound signals, wherein the processor is further configured to switch to the first mode in response to the indication of signal reliability corresponding to the sensed signal being a reliable signal, wherein the first mode comprises determining an ensemble averaged heart sound signal dependent on the cardiac electrical signal.

12. The device of claim 11, wherein the processor is further configured to switch to the second mode in response to the indication of signal reliability corresponding to the sensed signal being a not reliable signal, wherein the second mode comprises detecting a plurality of heart sounds from the heart sound signal independent of the cardiac electrical signal.

13. The device of claim 12, wherein the processor is further configured to detect whether a heart rate is greater than a detection threshold for a predetermined number of detection intervals less than a number of intervals to detect a treatable cardiac event.

14. The device of claim 12, wherein the processor is further configured to detect a plurality of heart sounds within the heart sound signal, determine a feature of each of the detected heart sounds of the plurality of heart sounds, classify each of the detected heart sounds as one of normal and abnormal, and generate an indication of a treatable rhythm in response to classifying at least M of a last N detected heart sounds as abnormal.

15. The device of claim 11, wherein determining the ensemble averaged heart sound signal comprises selecting an ensemble averaging interval in response to the cardiac electrical signal.

16. The device of claim 11, wherein the processor is further configured to determine a feature of the cardiac electrical signal corresponding to a cardiac cycle in response to an indication that the cardiac electrical signal is reliable, and determine whether to accept the cardiac cycle for inclusion in the ensemble averaged heart sound signal in response to the determined feature.

17. The device of claim 16, wherein the processor is further configured to determine a running average of a plurality of RR intervals, compare the running average to the current RR interval, and accept the cardiac cycle in response to a difference between the running average and the current RR interval being less than an acceptability threshold.

18. The device of claim 11, wherein the processor is further configured to determine a number of averaging intervals to be included in the ensemble averaged signal in response to an indication that the cardiac electrical signal is reliable, the number of averaging intervals corresponding to a required number of RR intervals to detect a tachyarrhythmia, determine the ensemble averaged signal in response to the determined number of averaging intervals, compare the heart sound feature determined from the ensemble averaged signal to a previously established baseline heart sound feature value, and generate an indication of a treatable rhythm in response to the heart sound feature determined from the ensemble averaged signal representing greater than a threshold percentage change from the established baseline heart sound feature value.

19. A medical device for detecting cardiac events, comprising:
a plurality of electrodes to sense cardiac electrical signals representative of electrical activity of a heart of a patient;
a processor configured to detect a cardiac event in response to the sensed cardiac signals, determine an indication of signal reliability corresponding to the sensed cardiac signals as being one of a reliable signal and a not reliable signal, and switch operation between a first mode of determining whether the sensed signal is one of treatable and not treatable and a second mode of determining whether the sensed signal is one of treatable and not treatable in response to the determined indication of signal reliability; and
a heart sound sensor to sense heart sounds and generate heart sounds signals representative of the sensed heart sound signals, wherein the processor is further configured to switch to the second mode in response to the indication of signal reliability corresponding to the sensed signal being a not reliable signal, wherein the second mode comprises detecting a plurality of heart sounds from the heart sound signal independent of the cardiac electrical signal.

20. A medical device for detecting cardiac events, comprising:
a plurality of electrodes to sense cardiac electrical signals representative of electrical activity of a heart of a patient; and
a processor configured to detect a cardiac event in response to the sensed cardiac signals, determine an indication of signal reliability corresponding to the sensed cardiac signals as being one of a reliable signal and a not reliable signal, and switch operation between a first mode of determining whether the sensed signal is one of treatable and not treatable and a second mode of determining whether the sensed signal is one of treatable and not treatable in response to the determined indication of signal reliability, wherein the processor is further configured to detect whether a heart rate is greater than a detection threshold for a predetermined number of detection intervals less than a number of intervals to detect a treatable cardiac event.

21. A non-transitory computer-readable medium storing a set of instructions for causing a processor in a medical device system to perform a method, comprising:
- sensing cardiac electrical signals representative of electrical activity of a heart of a patient;
- detecting a cardiac event in response to the sensed cardiac signals;
- determining an indication of signal reliability corresponding to the sensed cardiac signals as being one of a reliable signal and a not reliable signal;
- switching operation of the device between a first mode of determining whether the sensed signal is one of treatable and not treatable and a second mode of determining whether the sensed signal is one of treatable and not treatable in response to the determined indication of signal reliability;
- sensing heart sounds and generating heart sounds signals representative of the sensed heart sound signals;
- switching to the first mode in response to the indication of signal reliability corresponding to the sensed signal being a reliable signal, wherein the first mode comprises determining an ensemble averaged heart sound signal dependent on the cardiac electrical signal; and
- switching to the second mode in response to the indication of signal reliability corresponding to the sensed signal being a not reliable signal, wherein the second mode comprises detecting a plurality of heart sounds from the heart sound signal independent of the cardiac electrical signal.

\* \* \* \* \*